United States Patent [19]

Linz et al.

[11] Patent Number: 5,231,083
[45] Date of Patent: Jul. 27, 1993

[54] METHOD FOR THE TREATMENT OF CARDIAC AND OF VASCULAR HYPERTROPHY AND HYPERPLASIA

[75] Inventors: Wolfgang Linz, Mainz; Bernward Schölkens, Kelkheim; Wolfgang Scholz, Eschborn; Gabriele Wiemer; Hansjörg Urbach, both of Kronberg/Taunus; Rainer Henning, Hattersheim; Volker Teetz, Hofheim am Taunus, all of Fed. Rep. of Germany

[73] Assignee: Hoechst Aktiengesellschaft, Frankfurt am Main, Fed. Rep. of Germany

[21] Appl. No.: 564,618

[22] Filed: Aug. 9, 1990

[30] Foreign Application Priority Data

Aug. 11, 1989 [DE] Fed. Rep. of Germany ....... 3926606

[51] Int. Cl.$^5$ .......................... A61E 37/02; C07K 5/06
[52] U.S. Cl. ......................................... 514/19; 514/89;
514/91; 514/92; 514/212; 514/218; 514/312;
514/338; 514/223.5; 514/249; 514/255;
514/278; 514/318; 514/343; 514/409; 514/422;
514/423; 514/616; 514/693
[58] Field of Search ........................ 514/19, 89, 91, 92,
514/94, 171, 212, 218, 312, 338, 223.5, 249, 255,
278, 318, 343, 409, 422, 423, 616, 693

[56] References Cited

U.S. PATENT DOCUMENTS

| | | | |
|---|---|---|---|
| 4,311,705 | 1/1982 | Ondetti et al. | 514/422 |
| 4,337,201 | 6/1982 | Petrillo, Jr. | 548/413 |
| 4,374,829 | 2/1983 | Harris et al. | 514/21 |
| 4,381,297 | 4/1983 | Karanewsk et al. | 548/413 |
| 4,472,380 | 9/1984 | Harris et al. | 514/2 |
| 4,548,941 | 10/1985 | Halczenko et al. | 514/295 |
| 4,587,253 | 5/1986 | Halczenko et al. | 514/289 |
| 4,599,341 | 7/1986 | Halczenko et al. | 514/282 |
| 4,602,002 | 7/1986 | Patchett et al. | 514/616 |
| 4,656,188 | 4/1987 | Veber et al. | 514/423 |

Primary Examiner—Lester L. Lee
Attorney, Agent, or Firm—Finnegan, Henderson, Farabow, Garrett & Dunner

[57] ABSTRACT

The invention relates to a method for the treatment of cardiac and of vascular hypertrophy and hyperplasia by administration of angiotensin converting enzyme inhibitors. Administration of compounds of the formula I

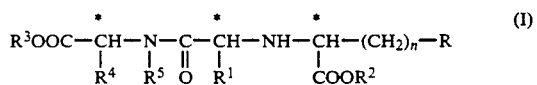

in which n is 1 or 2, R, $R^1$, $R^2$ and $R^3$ are identical or different and each is hydrogen or an organic radical, and $R^4$ and $R^5$ form, together with the atoms carrying them, a mono-, bi- or tricyclic heterocyclic ring system, is preferred. The invention additionally relates to angiotensin converting enzyme inhibitors and to agents containing these for administration for the treatment of the abovementioned diseases.

14 Claims, No Drawings

METHOD FOR THE TREATMENT OF CARDIAC AND OF VASCULAR HYPERTROPHY AND HYPERPLASIA

The invention relates to a method for the treatment of cardiac and of vascular hypertrophy and/or hyperplasia by oral or parenteral administration of compounds which inhibit angiotensin converting enzyme.

Particularly suitable in this connection are compounds of the formula I

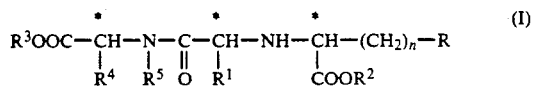

in which n is 1 or 2,

- R is hydrogen, an optionally substituted aliphatic radical with 1-8 carbon atoms, an optionally substituted alicyclic radical with 3-9 carbon atoms, an optionally substituted aromatic radical with 6-12 carbon atoms, an optionally substituted araliphatic radical with 7-14 carbon atoms, an optionally substituted alicyclicaliphatic radical with 7-14 carbon atoms or a radical $OR^a$ or $SR^a$ in which
- $R^1$ is an optionally substituted aliphatic radical with 1-4 carbon atoms, an optionally substituted aromatic radical with 6-12 carbon atoms or an optionally substituted heteroaromatic radical with 5-12 ring atoms,
- $R^1$ is hydrogen, an optionally substituted aliphatic radical with 1-6 carbon atoms, an optionally substituted alicyclic radical with 3-9 carbon atoms, an optionally substituted alicyclic-aliphatic radical with 4-13 carbon atoms, an optionally substituted aromatic radical with 6-12 carbon atoms, an optionally substituted araliphatic radical with 7-16 carbon atoms, an optionally substituted heteroaromatic radical with 5-12 ring atoms or the side-chain, which is protected where necessary, of a naturally occurring α-amino acid,
- $R^2$ and $R^3$ are identical or different and are hydrogen, an optionally substituted aliphatic radical with 1-6 carbon atoms, an optionally substituted alicyclic radical with 3-9 carbon atoms, an optionally substituted aromatic radical with 6-12 carbon atoms, an optionally substituted araliphatic radical with 7-16 carbon atoms and
- $R^4$ and $R^5$ form, together with the atoms carrying them, a heterocyclic mono-, bi- or tricyclic ring system with 4 to 15 carbon atoms.

Particularly suitable ring systems of this type are those from the following group: tetrahydroisoquinoline (A); decahydroisoquinoline (B); octahydroindole (C); octahydrocyclopenta[b]pyrrole (D); 2-azaspiro[4.5]decane (E); 2-azaspiro[4.4]nonane (F); spiro[(bicyclo[2.2.1-]heptane)-2,3'-pyrrolidine] (G); spiro[(bicyclo[2.2.2]octane)-2,3'-pyrrolidine] (H); 2-azatricyclo[4,3,0,1$^{6,9}$]decane (I); decahydrocyclohepta[b]pyrrole (J); octahydroisoindole (L); octahydrocyclopenta[c]pyrrole (M); 2,3,3a,4,5,7a-hexahydroindole (N); 2-azabicyclo[3.1.0-]hexane (K); all of which can optionally be substituted. However, the unsubstituted systems are preferred.

In the case of compounds which contain several chiral atoms, all possible diastereomers as racemates or enantiomers, or mixtures of various diastereomers, are suitable.

The suitable cyclic amino acid esters have the following structural formulae.

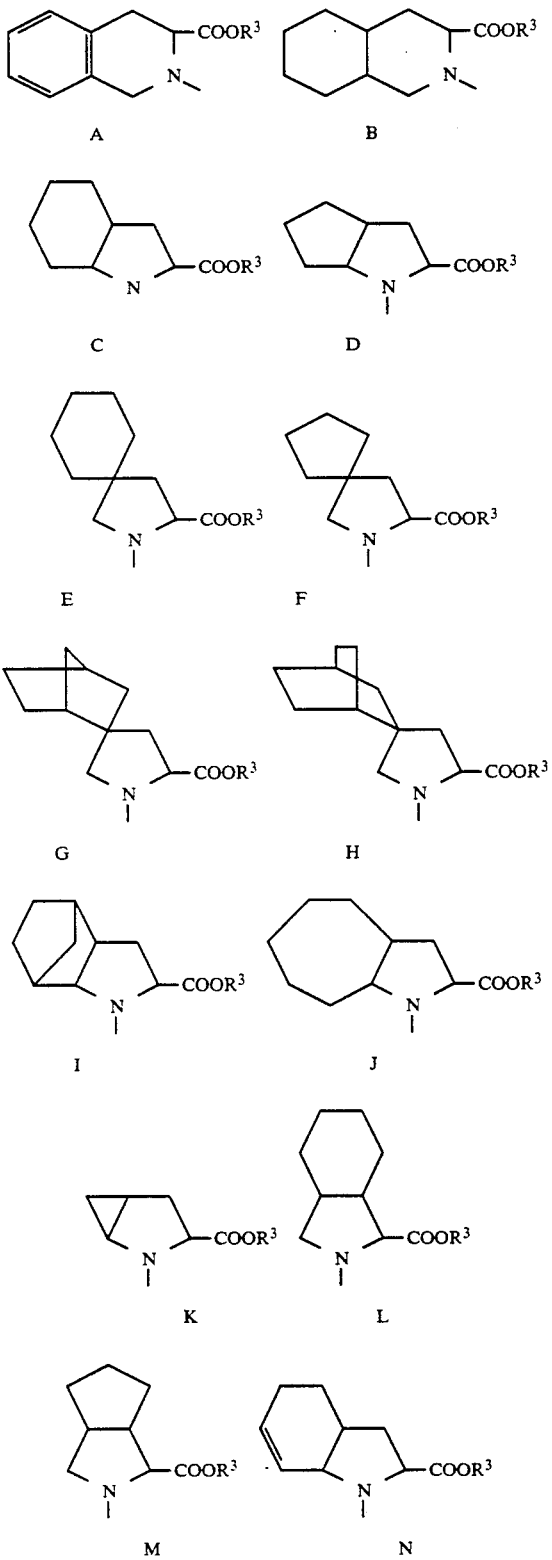

A preferred embodiment comprises using compounds of the formula I in which n is 1 or 2, R is hydrogen, alkyl with 1–8 carbon atoms, alkenyl with 2–6 carbon atoms, cycloalkyl with 3–9 carbon atoms, aryl which has 6–12 carbon atoms and can be mono-, di- or trisubstituted by ($C_1$–$C_4$)-alkyl, ($C_1$–$C_4$)-alkoxy, hydroxyl, halogen, nitro, amino, aminomethyl, ($C_1$–$C_4$)-alkylamino, di-($C_1$–$C_4$)-alkylamino, ($C_1$–$C_4$)-alkanoylamino, methylenedioxy, carboxyl, cyano and/or sulfamoyl, alkoxy with 1–4 carbon atoms, aryloxy which has 6–12 carbon atoms and can be substituted as described above for aryl, mono- or bicyclic heteroaryloxy which has 5–7 or 8–10 ring atoms, of which 1 to 2 ring atoms are sulfur or oxygen atoms and/or 1 to 4 ring atoms are nitrogen, and which can be substituted as described above for aryl, amino-($C_1$–$C_4$)-alkyl, ($C_1$–$C_4$)-alkanoylamino-($C_1$$C_4$)-alkyl, ($C_7$–$C_{13}$)-aroylamino-($C_1$–$C_4$)-alkyl, ($C_1$–$C_4$)-alkoxycarbonylamino-($C_1$–$C_4$) alkyl, ($C_6$–$C_{12}$)-aryl-($C_1$–$C_4$)-alkoxycarbonylamino-($C_1$–$C_4$)alkyl, ($C_6$–$C_{12}$)-aryl-($C_1$–$C_4$)alkylamino-($C_1$–$C_4$)-alkyl, ($C_1$–$C_4$)-alkyl-amino-($C_1$–$C_4$)-alkyl, di-($C_1$–$C_4$)-alkylamino-($C_1$–$C_4$)-alkyl, guanidino-($C_1$–$C_4$)-alkyl, imidazolyl, indolyl, ($C_1$–$C_4$)-alkylthio, ($C_1$–$C_4$)-alkylthio-($C_1$–$C_4$)-alkyl, ($C_6$–$C_{12}$)-arylthio-($C_1$–$C_4$)-alkyl which can be substituted in the aryl moiety as described above for aryl, ($C_6$–$C_{12}$)-aryl-($C_1$–$C_4$)-alkylthio which can be substituted in the aryl moiety as described above for aryl, carboxy-($C_1$–$C_4$)-alkyl, carboxyl, carbamoyl, carbamoyl-($C_1$–$C_4$)-alkyl, ($C_1$–$C_4$)-alkoxycarbonyl-($C_1$–$C_4$)-alkyl, ($C_6$–$C_{12}$)-aryloxy-($C_1$–$C_4$)-alkyl which can be substituted in the aryl moiety as described above for aryl, or ($C_6$–$C_{12}$)-aryl-($C_1$–$C_4$)-alkoxy which can be substituted in the aryl moiety as described above for aryl, $R^1$ is hydrogen, alkyl with 1–6 carbon atoms, alkenyl with 2–6 carbon atoms, alkynyl with 2–6 carbon atoms, cycloalkyl with 3–9 carbon atoms, cycloalkenyl with 5–9 carbon atoms, ($C_3$–$C_9$)-cycloalkyl-($C_1$–$C_4$)-alkyl, ($C_5$–$C_9$)-cycloalkenyl-($C_1$–$C_4$)alkyl, optionally partially hydrogenated aryl which has 6–12 carbon atoms and can be substituted as described above for R, ($C_6$–$C_{12}$)-aryl-($C_1$–$C_4$)-alkyl or ($C_7$–$C_{13}$)-aroyl-($C_1$ or $C_2$)-alkyl, both of which can be substituted like the aryl above, mono- or bicyclic, optionally partially hydrogenated heteroaryl which has 5–7 or 8–10 ring atoms, of which 1 to 2 ring atoms are sulfur or oxygen atoms and/or 1 to 4 ring atoms are nitrogen atoms, and which can be substituted like the aryl above, or the optionally protected side-chain of a naturally occurring α-amino acid $R^1$—CH(NH$_2$)—COOH, $R^2$ and $R^3$ are identical or different and are hydrogen, alkyl with 1–6 carbon atoms, alkenyl with 2–6 carbon atoms, di-($C_1$–$C_4$)-alkylamino-($C_1$–$C_4$)-alkyl, ($C_1$–$C_5$)-alkanoyloxy-($C_1$–$C_4$)-alkyl, ($C_1$–$C_6$)-alkoxycarbonyloxy-($C_1$–$C_4$)-alkyl, ($C_7$–$C_{13}$)-aroyloxy-($C_1$–$C_4$)-alkyl, ($C_6$–$C_{12}$)-aryloxycarbonyloxy($C_1$–$C_4$)-alkyl, aryl with 6–12 carbon atoms, ($C_6$–$C_{12}$)-aryl-($C_1$–$C_4$)alkyl, ($C_3$–$C_9$)-cycloalkyl or ($C_3$–$C_9$)-cycloalkyl-($C_1$–$C_4$)-alkyl, and $R^4$ and $R^5$ have the abovementioned meaning.

A particularly preferred embodiment comprises using compounds of the formula I in which n is 1 or 2, R is ($C_1$–$C_6$)-alkyl, ($C_2$–$C_6$)-alkenyl, ($C_3$–$C_9$)-cycloalkyl, amino-($C_1$–$C_4$)-alkyl, ($C_2$–$C_5$)-acylamino-($C_1$–$C_4$)-alkyl, ($C_7$–$C_{13}$)-aroylamino-($C_1$–$C_4$)-alkyl, ($C_1$–$C_4$)-alkoxycarbonylamino-($C_1$–$C_4$) -alkyl, (6–$C_{12}$)-aryl-($C_1$–$C_4$)-alkoxycarbonylamino-($C_1$–$C_4$)-alkyl, ($C_6$–$C_{12}$)-aryl which can be mono-, di- or trisubstituted by ($C_1$–$C_4$)-alkyl, ($C_1$–$C_4$)-alkoxy, hydroxyl, halogen, nitro, amino, ($C_1$–$C_4$)-alkylamino, di-($C_1$–$C_4$)-alkylamino and/or methylenedioxy, or 3-indolyl, in particular methyl, ethyl, cyclohexyl, tert. butoxycarbonylamino-($C_1$–$C_4$)-alkyl, benzoyloxycarbonylamino-($C_1$–$C_4$)-alkyl or phenyl which can be mono- or disubstituted by phenyl, ($C_1$–$C_2$)-alkyl, ($C_1$ or $C_2$)-alkoxy, hydroxyl, fluorine, chlorine, bromine, amino, ($C_1$–$C_4$)-alkylamino, di($C_1$–$C_4$)-alkylamino, nitro and/or methylenedioxy or, in the case of methoxy, trisubstituted, $R^1$ is hydrogen or ($C_1$–$C_6$)-alkyl which can optionally be substituted by amino, ($C_1$–$C_6$)-acylamino or benzoylamino, or ($C_2$–$C_6$)-alkenyl, ($C_3$–$C_9$)-cycloalkyl, ($C_5$–$C_9$)-cycloalkenyl, ($C_3$–$C_7$)-cycloalkyl-($C_1$–$C_4$)-alkyl, ($C_6$–$C_{12}$)-aryl or partially hydrogenated aryl, each of which can be substituted by ($C_1$–$C_4$)-alkyl, ($C_1$ or $C_2$)alkoxy or halogen, or ($C_6$–$C_{12}$)-aryl-($C_1$ to $C_4$)-alkyl or ($C_7$–$C_{13}$)-aroyl-($C_1$–$C_2$)-alkyl, both of which can be substituted in the aryl radical as defined above, or a mono- or bicyclic heterocyclic radical with 5 to 7 or 8 to 10 ring atoms, of which 1 to 2 ring atoms are sulfur or oxygen atoms and/or 1 to 4 ring atoms are nitrogen atoms, or a side-chain of a naturally occurring, optionally protected α-amino acid, but in particular hydrogen, ($C_1$–$C_3$)-alkyl, ($C_2$ or $C_3$)-alkenyl, the optionally protected side-chain of lysine, benzyl, 4-methoxybenzyl, 4-ethoxybenzyl, phenethyl, 4-aminobutyl or benzoylmethyl, $R^2$ and $R^3$ are identical or different radicals and are hydrogen, ($C_1$–$C_6$)-alkyl, ($C_2$–$C_6$)-alkenyl or ($C_6$–$C_{12}$)-aryl-($C_1$–$C_4$)-alkyl, but in particular hydrogen, ($C_1$–$C_4$)-alkyl or benzyl, and $R^4$ and $R^5$ have the abovementioned meaning.

Particularly preferred is the use of compounds of the formula I in which n is 2, R is phenyl, $R^1$ is methyl, $R^2$ and $R^3$ are identical or different ($C_1$–$C_6$)-alkyl radicals or ($C_7$–$C_{10}$)-aralkyl radicals such as benzyl or nitrobenzyl, and $R^4$ and $R^5$ together are a radical of the formula

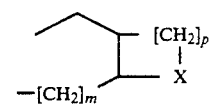

in which m is 0 or 1, p is 0, 1 or 2 and X is —CH$_2$—, —CH$_2$—CH$_2$— or —CH=CH—, it also being possible for a 6-membered ring formed with X to be a benzene ring.

Aryl preferably means here and hereinafter optionally substituted phenyl, biphenylyl or naphthyl. A corresponding statement applies to radicals derived from aryl, such as aryloxy and arylthio. Aroyl particularly means benzoyl. Aliphatic radicals can be straight-chain or branched.

Examples of the meaning of a mono- or bicyclic heterocyclic radical with 5 to 7 or 8 to 10 ring atoms, of which 1 to 2 ring atoms are sulfur or oxygen atoms and/or of which 1 to 4 ring atoms are nitrogen atoms, are thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl and isothiazolyl. These radicals can also be partially or completely hydrogenated.

Naturally occurring α-amino acids are described, for example, in Houben-Weyl, Methoden der Organischen Chemie (Methods of Organic Chemistry) Vol. XV/1 and XV/2.

If $R^1$ is a side-chain of a protected naturally occurring α-amino acid, such as, for example, protected Ser, Thr, Asp, Asn, Glu, Gln, Arg, Lys, Hyl, Cys, Orn, Cit, Tyr, Trp, His or Hyp, preferred protective groups are the groups customary in peptide chemistry (cf. Houben-Weyl, Vol. XV/1 and XV/2). In the case where $R^1$ is the protected lysine side-chain, the known amino protective groups, but in particular Z, Boc or $(C_1-C_6)$-alkanoyl, are preferred. Suitable and preferred O-protective groups for tyrosine are $(C_1-C_6)$-alkyl, in particular methyl or ethyl.

The following compounds can be particularly advantageously used in the method according to the invention:

N-(1-S-Carbethoxy-3-phenyl-propyl)-S-alanyl-S-1,2,3,4-tetrahydroisoquinoline-3-carboxylic acid
N-(1-S-Carbethoxy-3-cyclohexyl-propyl)-S-alanyl-S-1,2,3,4-tetrahydroisoquinoline-3-carboxylic acid
N-(1-S-Carbethoxy-3-phenyl-propyl)-S-lysyl-S-1,2,3,4-tetrahydroisoquinoline-3-carboxylic acid
N-(1-S-Carbethoxy-3-phenyl-propyl)-O-ethyl-S-tyrosyl-S-1,2,3,4-tetrahydroisoquinoline-3-carboxylic acid
N-(1-S-Carbethoxy-3-phenyl-propyl)-S-alanyl-3S-decahydroisoquinoline-3-carboxylic acid
N-(1-S-Carbethoxy-3-phenyl-propyl)-S-alanyl-(2S,3aS,7aS)-octahydroindole-2-carboxylic acid
N-(1-S-Carbethoxy-3-cyclohexyl-propyl)-S-alanyl-(2S,3aS,7aS)-octahydroindole-2-carboxylic acid
N-(1-S-Carbethoxy-3-phenyl-propyl)-S-lysyl-(2S,3aS,7aS)-octahydroindole-2-carboxylic acid
N-(1-S-Carbethoxy-3-cyclohexyl-propyl)-S-lysyl-(2S,3aS,7aS)-octahydroindole-2-carboxylic acid
N-(1-S-Carbethoxy-3-cyclohexyl-propyl)-S-lysyl-(2S,3aS,7aS)-octahydroindole-2-carboxylic acid
N-(1-S-Carbethoxy-3-phenyl-propyl)-O-methyl-S-tyrosyl-(2S,3aS,7aS)-octahydroindole-2-carboxylic acid
N-(1-S-Carbethoxy-3-phenyl-propyl)-O-ethyl-S-tyrosyl-(2S,3aS,7aS)-octahydroindole-2-carboxylic acid
N-(1-S-Carbethoxy-3-(3,4-dimethylphenyl-propyl)-S-alanyl-(2S,3aS,7aS)-octahydroindole-2-carboxylic acid
N-[1-S-Carbethoxy-3-(4-fluorophenyl)-propyl]-S-alanyl-(2S,3aS,7aS)-octahydroindole-2-carboxylic acid
N-[1-S-Carbethoxy-3-(4-methoxyphenyl)-propyl]-S-alanyl-(2S,3aS,7aS)-octahydroindole-2-carboxylic acid
N-[1-S-Carbethoxy-3-(3,4-dimethoxyphenyl)-propyl]-S-alanyl-(2S,3aS,7aS)-octahydroindole-2-carboxylic acid
N-(1-S-Carbethoxy-3-cyclopentylpropyl)-S-alanyl-(2S,3aS,7aS)-octahydroindole-2-carboxylic acid
N-(1-S-Carbethoxy-3-phenyl-propyl)-S-alanyl-(2S,3aR,7aS)-octahydroindole-2-carboxylic acid
N-(1-S-Carbethoxy-3-cyclohexyl-propyl)-S-alanyl-(2S,3aR,7aS)-octahydroindole-carboxylic acid
N-(1-S-Carbethoxy-3-phenyl-propyl)-S-lysyl-(2S,3aR,7aS)-hydroindole-2-carboxylic acid
N-(1-S-Carbethoxy-3-cyclohexyl-propyl)-S-lysyl-(2S,3aR,7aS)-octahydroindole-2-carboxylic acid
N-(1-S-Carbethoxy-3-phenyl-propyl)-O-ethyl-S-tyrosyl-(2S,3aS,7aR)-octahydroindole-2-carboxylic acid
N-(1-S-Carbethoxy-3-phenyl-propyl)-S-alanyl-(2S,3aR,7aR)-octahydroindole-2-carboxylic acid
N-(1-S-Carbethoxy-3-phenyl-propyl)-S-lysyl-(2S,3aR,7aS)-octahydroindole-2-carboxylic acid
N-(1-S-Carbethoxy-3-cyclohexyl-propyl)-S-alanyl-(2S,3aR,7aR)-octahydroindole-2-carboxylic acid
N-(1-S-Carbethoxy-3-cyclohexyl-propyl)-O-ethyl-S-tyrosyl-(2S,3aR,7aR)-octahydroindole-2-carboxylic acid
N-(1-S-Carbethoxy-3-phenyl-propyl)-S-alanyl-(2S,3aS,7aR)-octahydroindole-2-carboxylic acid
N-(1-S-Carbethoxy-3-phenyl-propyl)-O-ethyl-S-tyrosyl-(2S,3aS,7aS)-octahydroindole-2-carboxylic acid
N-(1-S-Carbethoxy-3,4-dimethylphenyl-propyl)-S-alanyl-(2S,3aS,7aS)-octahydroindole-2-carboxylic acid
N-[1-S-Carbethoxy-3-(4-fluorophenyl)-propyl]-S-alanyl-(2S,3aS,7aS)-octahydroindole-2-carboxylic acid
N-[1-S-Carbethoxy-3-(4-methoxyphenyl)-propyl]-S-alanyl-(2S,3aS,7aS)-octahydroindole-2-carboxylic acid
N-[1-S-Carbethoxy-3-(3,4-dimethoxyphenyl)-propyl]-S-alanyl-(2S,3aS,7aS)-octahydroindole-2-carboxylic acid
N-(1-S-Carbethoxy-3-cyclopentylpropyl)-S-alanyl-(2S,3aS,7aS)-octahydroindole-2-carboxylic acid
N-(1-S-Carbethoxy-3-phenyl-propyl)-S-alanyl-cis-endo-2-azabicyclo[3.3.0]octane-3-S-carboxylic acid
N-(1-S-Carbethoxy-3-phenyl-propyl)-S-lysyl-cis-endo-2-azabicyclo[3.3.0]octane-3-S-carboxylic acid
N-(1-S-Carbethoxy-3-cyclohexyl-propyl)-S-alanyl-cis-endo-2-azabicyclo[3.3.0]octane-3-S-carboxylic acid
N-(1-S-Carboxy-3-cyclohexyl-propyl)-S-alanyl-cis-endo-2-azabicyclo[3.3.0]octane-2-S-carboxylic acid
N-(1-S-Carbethoxy-butyl)-S-alanyl-cis-endo-2-azabicyclo[3.3.0]octane-3-S-carboxylic acid
N-(1-S-Carbethoxy-3-(3,4-dimethoxyphenylpropyl)-S-alanyl-cis-endo-2-azabicyclo[3.3.0]octane-3-S-carboxylic acid
N-(1-S-Carbethoxy-3-cyclopentyl-propyl)-S-alanyl-cis-endo-azabicyclo[3.3.0]octane-3-S-carboxylic acid
N-(1-S-Carbethoxy-3-phenyl-propyl)-O-methyl-S-tyrosyl-cis-endo-2-azabicyclo[3.3.0]octane-3-S-carboxylic acid
N-(1-S-Carbethoxy-3-phenyl-propyl)-O-ethyl-S-tyrosyl-cis-endo-2-azabicyclo[3.3.0]octane-3-S-carboxylic acid
N-(1-S-Carbethoxy-3-(4-fluorophenyl-propyl)-S-alanyl-cis-endo-azabicyclo[3.3.0]octane-3-S-carboxylic acid
N-(1-S-Carbethoxy-3-(4-methoxyphenyl-propyl)-S-alanyl-cis-endo-2-azabicyclo[3.3.0]octane-3-S-carboxylic acid
N-(1-S-Carbethoxy-3-phenyl-propyl)-S-lysyl-(2S,3aR,6aS)-octahydrocyclopenta[b]pyrrole-2-carboxylic acid
N-(1-S-Carbethoxy-3-cyclohexylpropyl)-lysyl-(2S,3aR,6aS)-octahydrocyclopenta[b]pyrrole-2-carboxylic acid
N-(1-S-Carbethoxy-3-phenyl-propyl)-O-ethyl-S-tyrosyl-(2S,3aR,6aS)-octahydrocyclopenta[b]pyrrole-2-carboxylic acid
N-(1-S-Carbethoxy-3-phenyl-propyl)-S-alanyl-2-(2S,3aR,6aS)-octahydrocyclopenta[b]pyrrole-2-carboxylic acid N-(1-S-Carbethoxy-3-phenyl-propyl)-S-alanyl-2-azaspiro[4,5]decane-3-S-carboxylic acid
N-(1-S-Carbethoxy-3-phenyl-propyl)-O-ethyl-2-tyrosyl-azaspiro-[4,5]decane-3-S-carboxylic acid
N-(1-S-Carbethoxy-3-phenyl-propyl)-S-lysyl-2-azaspiro[4,5]decane-3-S-carboxylic acid
N-(1-S-Carbethoxy-3-cyclohexylpropyl)-S-alanyl-2-aza-spiro-[4,5]decane-3-S-carboxylic acid
N-(1-S-Carbethoxy-3-cyclohexylpropyl)-S-lysyl-2-azaspiro[4,5]decane-3-S-carboxylic acid
N-(1-S-Carbethoxy-3-phenyl-propyl)-S-alanyl-2-azaspiro[4,4]nonane-3-S-carboxylic acid
N-(1-S-Carbethoxy-3-phenyl-propyl)-O-ethyl-S-tyrosyl-2-azaspiro[4,4]nonane-3-S-carboxylic acid
N-(1-S-Carbethoxy-3-phenyl-propyl)-S-lysyl-2-azaspiro-[4,4]nonane-3-S-carboxylic acid
N-(1-S-Carbethoxy-3-cyclohexyl-propyl)-S-alanyl-2-azaspiro[4,4]nonane-3-S-carboxylic acid
N-(1-S-Carbethoxy-3-cyclopentyl-propyl)-S-alanyl-2-azaspiro[4,4]nonane-3-S-carboxylic acid
N-(1-S-Carbethoxy-3-cyclopentyl-propyl)-S-lysyl-2-azaspiro[4,4]nonane-3-S-carboxylic acid
N-(1-S-Carbethoxy-3-phenyl-propyl)-S-alanyl-spiro[bicyclo[2.2.1]heptane-2,3'-pyrrolidine]-5'-S-carboxylic acid
N-(1-S-Carbethoxy-3-phenyl-propyl)-O-ethyl-S-tyrosylspiro[bicyclo[2.2.1]heptane-2,3'-pyrrolidine]-5'-S-carboxylic acid
N-(1-S-Carbethoxy-3-phenyl-propyl)-S-lysyl-spiro[bicyclo[2.2.1]heptane-2,3'-pyrrolidine]-5'-S-carboxylic acid
N-(1-S-Carbethoxy-3-cyclohexyl-propyl)-S-alanyl-spiro[bicyclo[2.2.1]heptane-2,3'-pyrrolidine]5'-S-carboxylic acid
N-(1-S-Carbethoxy-3-cyclohexyl-propyl)-S-lysyl-spiro[bicyclo[2.2.1]heptane-2,3'-pyrrolidine]-5'-S-carboxylic acid
N-(1-S-Carbethoxy-3-phenyl-propyl)-S-alanyl-spiro[bicyclo[2.2.2]octane-2,3'-pyrrolidine]-5'-S-carboxylic acid
N-(1-S-Carbethoxy-3-phenyl-propyl)-O-ethyl-tyrosyl-spiro[bicyclo[2.2.2]octane-2,3'-pyrrolidine]-5'-S-carboxylic acid
N-(1-S-Carbethoxy-3-phenyl-propyl)-S-lysyl-spiro[bicyclo[2.2.2]octane-2,3'-pyrrolidine]-5'-S-carboxylic acid
N-(1-S-Carbethoxy-3-cyclohexyl-propyl)-S-alanyl-spiro[bicyclo[2.2.2]octane-2,3'-pyrrolidine]-5'-S-carboxylic acid
N-(1-S-Carbethoxy-3-phenyl-propyl)-S-alanyl-2-azatricyclo[4,3,0,1$^{6,9}$]decane-3-S-carboxylic acid
N-(1-S-Carbethoxy-3-phenyl-propyl)-O-ethyl-S-tyrosyl-2-azatricyclo[4,3,0,1$^{6,9}$]decane-3-S-carboxylic acid
N-(1-S-Carbethoxy-3-phenyl-propyl)-S-lysyl-2-azatricyclo[4,3,0,1$^{6,9}$]decane-3-S-carboxylic acid
N-(1-S-Carbethoxy-3-cyclohexyl-propyl)-S-alanyl-2-azatricyclo[4,3,0,1$^{6,9}$]decane-3-S-carboxylic acid
N-(1-S-Carbethoxy-3-cyclohexyl-propyl)-S-lysyl-2-azatricyclo[4,3,0,1$^{6,9}$]decane-3-S-carboxylic acid
N-(1-S-Carbethoxy-3-phenyl-propyl)-S-alanyl-decahydrocyclohepta[b]pyrrole-2-S-carboxylic acid
N-(1-S-Carbethoxy-3-phenyl-propyl)-O-ethyl-S-tyrosyldecahydrocyclohepta[b]pyrrole-2-S-carboxylic acid
N-(1-S-Carbethoxy-3-phenyl-propyl)-S-lysyl-decahydrocyclohepta[b]pyrrole-2-S-carboxylic acid
N-(1-S-Carbethoxy-3-cyclohexyl-propyl)-S-alanyl-decahydrocyclohepta[b]pyrrole-2-S-carboxylic acid
N-(1-S-Carbethoxy-3-cyclohexyl-propyl)-S-lysyl-decahyirocyclohepta[b]pyrrole-2-S-carboxylic acid
N-(1-S-Carbethoxy-3-phenyl-propyl)-S-alanyl-trans-octa-hydroisoindole-1-S-carboxylic acid
N-(1-S-Carbethoxy-3-phenyl-propyl)-S-alanyl-cis-octa-hydroisoindole-1-S-carboxylic acid
N-(1-S-Carbethoxy-3-cyclohexyl-propyl)-S-alanyl-trans-octahydroisoindole-1-S-carboxylic acid
N-(1-S-Carbethoxy-3-cyclohexyl-propyl)-S-alanyl-cis-octahydroisoindole-1-S-carboxylic acid
N-(1-S-Carbethoxy-3-phenyl-propyl)-S-alanyl-cis-octahydrocyclopenta[c]pyrrole-1-S-carboxylic acid
N-(1-S-Carbethoxy-3-cyclohexyl-propyl)-S-alanyl-cis-octahydrocyclopenta[c]pyrrole-1-S-carboxylic acid-benzyl ester
N-(1-S-Carbethoxy-3-cyclohexyl-propyl)-S-lysyl-cis-octahydrocyclopenta[c]pyrrole-1-S-carboxylic acid
N-(1-S-Carbethoxy-3-phenyl-propyl)-S-alanyl-2,3,3a,4,5,7a-hexahydroindole-cis-endo-2-S-carboxylic acid
N-(1-S-Carbethoxy-3-phenyl-propyl)-S-lysyl-2,3,3a,4,5,7a-hexahydroindole-cis-endo-2-S-carboxylic acid
N-(1-S-Carbethoxy-3-cyclohexyl-propyl)-S-lysyl-2-azabicyclo[3.1.0]hexane-3-S-carboxylic acid
N-(1-S-Carboxy-3-phenyl-propyl)-S-lysyl-2-azabicyclo[3.1.0]hexane-cis-endo-3-S-carboxylic acid
N-(1-S-Carbethoxy-3-cyclopentylpropyl)-S-alanyl-2-azabicyclo[3.1.0]hexane-3-carboxylic acid
N-(1-S-Carbethoxy-3-phenyl-propyl)-S-alanyl-cis-endo-2-azabicyclo[3.1.0]hexane-3-S-carboxylic acid
N-(1-S-Carbethoxy-3-cyclohexyl-propyl)-S-alanyl-cis-endo-2-azabicyclo[3.1.0]hexane-3-S-carboxylic acid These compounds can be prepared, for example, by the process described in German Patent Application P 3,333,455.2, in which the tert. butyl or benzyl radicals described in the application are converted in a known manner by acid or alkaline hydrolysis or by noble metal-catalyzed hydrogenolysis into the monocarboxylic acid derivatives. The N$^\epsilon$-benzyloxycarbonyl protective group of the lysine derivatives is removed by noble metal-catalyzed hydrogenolysis. The compounds listed above can easily be converted with physiologically tolerated acids or bases (in the case of mono- or dicarboxylic acids) into the corresponding salts (for example hydrochlorides, maleates, fumarates etc.) and used according to the invention as salts.

The compounds of the formula I are inhibitors of angiotensin converting enzyme (ACE) or intermediates for the preparation of inhibitors of this type, and can also be employed for controlling high blood pressure of a variety of etiologies. The compounds of the formula I are disclosed, for example, in U.S. Pat. No. 4,129,571, U.S. Pat. No. 4,374,829, EP-A-79,522, EP-A-79,022, EP-A-49,658, EP-A-51,301, U.S. Pat. No. 4,454,292, U.S. Pat. No. 4,374,847, EP-A-72,352, U.S. Pat. No. 4,350,704, EP-A-50,800, EP-A-46,953, U.S. Pat. No. 4,344,949, EP-A-84,164, U.S. Pat. No. 4,470,972, EP-A-65,301 and EP-A-52,991.

Also advantageous are orally effective ACE inhibitors such as, for example, ramipril, enalapril, captopril, lisinopril, perindopril, cilazapril, RHC 3659, CGS 13945, CGS 13928C, CGS 14824A, CI-906, SCH 31846, zofenopril, fosenopril, alacepril and others. Orally effective ACE inhibitors are described, for example, in Brunner et al., J. Cardiovasc. Pharmacol. 7 (Suppl. I) [1985]S2-S11.

Preferred ACE inhibitors are those of the formula III disclosed in EP-A-79,022

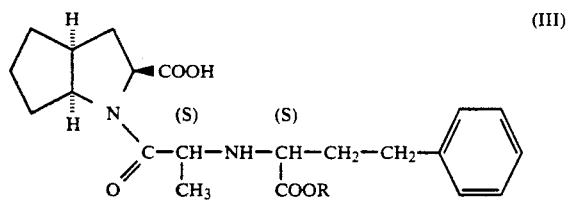

in which
R is hydrogen, methyl, ethyl or benzyl, in particular the compound of the formula III in which R is ethyl (ramipril).

Additionally preferred are the ACE inhibitors of the formula IV disclosed in EP-A-84,164

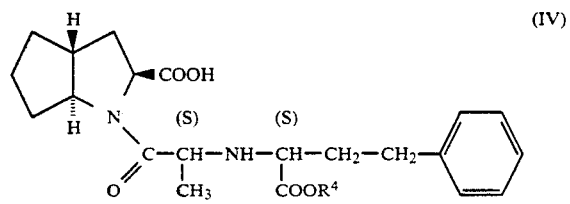

in which
$R^4$ is hydrogen, $(C_1-C_4)$-alkyl or benzyl, in particular the compound of the formula IV in which $R^4$ is ethyl.

Applying the method according to the invention, it is possible to adminster the angiotensin converting enzyme inhibitors described above to mammals such as monkeys, dogs, cats, rats, humans etc. The compounds suitable for the use according to the invention are expediently incorporated in a customary manner into pharmaceutical products. They can be converted into the customary administration forms such as capsules, tablets, coated tablets, solutions, ointments, emulsions and into depot form too. The active compound can also, where appropriate, be present in microencapsulated form. The products can contain tolerated organic or inorganic additives, for example granulating auxiliaries, adhesives and binders, lubricants, suspending agents, solvents, antibacterial agents, wetting agents and preservatives. Forms for oral and parenteral administration are preferred. The compounds of the formula I can be administered in doses of 0.001 mg/kg-20 mg/kg, in particular 0.005 mg/kg-1 mg/kg, once to three times a day.

Growth factors which lead to proliferation and to swelling of cells make a crucial contribution to the development of cardiac hypertrophy as a consequence of hypertension, and in the hypertrophy and hyperplasia of smooth muscles of vessels, as are observed in hypertension and in the development of atherosclerotic plaques.

It is known from the literature that angiotensin II is a growth factor of this type. Treatment of muscle cells with angiotensin II leads to stimulation of phospholipase C (J. Biol. Chem. 260, 8901 (1986)), to mobilization of intracellular calcium (Hypertension 7, 447 (1988)), to activation of $Na^+/H^+$ exchange (J. Biol. Chem. 262, 5057 (1987) and to activation of protein synthesis and induction of messenger RNA for the c-fos protooncogene (J. Biol. Chem. 264, 526 (1989)). Furthermore, angiotensin II potentiates the proliferative action of other growth factors such as PDGF and EGF (Amer. J. Physiol (1987), F 299). These described actions of angiotensin II are mainly elicited by locally synthesized peptide. Compounds capable of local prevention of the formation of angiotensin II ought therefore to have an action on hypertrophy and hyperplasia of smooth muscle of vessels, and of the myocardium. We have now found, surprisingly, that inhibitors of angiotensin converting enzyme are able to abolish the described trophic effects of angiotensin II even at doses at which they do not yet display an antihypertensive action.

The results with N-(1-S-carbethoxy-3-phenyl-propyl)-S-alanyl-cis-endo-2-azabicyclo[3.3.0]octane-3-S-carboxylic acid (formula II) in each case are to serve as examples hereinafter.

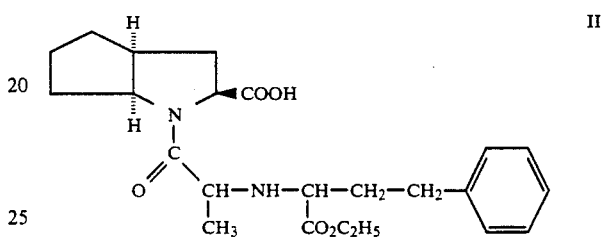

Description of experiments

Cardiac hypertrophy was generated in conscious rats by constriction of the abdominal aorta. Once this had been completely established, groups of the animals received 1 mg/kg/d (antihypertensive dose) or 10 μg/kg/d (nonantihypertensive dose) of the compound of the formula II by oral administration for 3 weeks. Control groups of animals which were not given the substance and which had undergone a sham operation were included. After the end of the 3 weeks, the animals were sacrificed, and the weight of the heart, the thickness of the left ventricle wall and the myocardial protein content were determined. The values obtained in the two treated groups were significantly reduced and indistinguishable from the controls which had undergone a sham operation.

The examples which follow indicate the forms to be administered for the treatment of cardiac and of vascular hypertrophy and hyperplasia by the method according to the invention. The compounds of the formula I can be converted into the forms appropriate for administration in analogy to the examples.

EXAMPLE 1

Preparation of the agent used according to the invention for oral administration in the treatment of cardiac and of vascular hypertrophy and hyperplasia. 1000 tablets which each contain 10 mg of 1-N-(1-S-carbethoxy-3-phenyl-propyl)-S-alanyl-1S,3S, 5S-2-azabicyclo[3.3.-0]octane-3-carboxylic acid are prepared with the following auxiliaries:

| | |
|---|---|
| N-(1-S-Carbethoxy-3-phenyl-propyl)-S-alanyl-1S,3S,5S-2-azabicyclo[3.3.0]octane-3-carboxylic acid | 10 g |
| Corn starch | 140 g |
| Gelatin | 7.5 g |
| Microcrystalline cellulose | 2.5 g |
| Magnesium stearate | 2.5 g |

N-(1-S-Carbethoxy-3-phenyl-propyl)-S-alanyl-1S,3S, 5S-2-azabicyclo[3.3.0]octane-3-carboxylic acid and corn starch are mixed with an aqueous gelatin solution. The mixture is dried and ground to granules. Microcrystalline cellulose and magnesium stearate are mixed with the granules. The resulting granules are compressed to 1000 tablets, each tablet containing 10 mg of the ACE inhibitor. These tablets can be used for the treatment of cardiac and of vascular hypertrophy and hyperplasia.

EXAMPLE 2

1000 tablets, each of which contains 1 mg of N-(1-S-carbethoxy-3-phenyl-propyl)-S-alanyl-1S,3S, 5S-2-azabicyclo[3.3.0]octane-3-carboxylic acid, are prepared in analogy to Example 1 by using 1 g of this compound in the mixture described in Example 1.

EXAMPLE 3

1000 tablets, each of which contains 10 mg of N-(1-S-carbethoxy-3-phenyl-propyl)-S-alanyl-(2S,3aR,7aS)-octa-hydroindole-2-carboxylic acid hydrochloride, are prepared in analogy to Example 1.

EXAMPLE 4

1000 tablets, each of which contains 1 mg of N-(1-S-carbethoxy-3-phenyl-propyl)-S-alanyl-(2S,3aR,7aS)-octa-hydroindole-2-carboxylic acid hydrochloride, are prepared in analogy to Example 2.

EXAMPLE 5

Gelatin capsules, each of which contains 10 mg of N-(1-S-carbethoxy-3-phenyl-propyl)-S-alanyl-1S,3S, 5S-2-azabicyclo[3.3.0]octane-3-carboxylic acid, are filled with the following mixture:

| | |
|---|---|
| N-(1-S-Carbethoxy-3-phenyl-propyl)-S-alanyl-1S,3S,5S-2-azabicyclo[3.3.0]octane-3-carboxylic acid | 10 mg |
| Magnesium stearate | 1 mg |
| Lactose | 214 mg |

These capsules can be used for the treatment of atherocardiac and of vascular hypertrophy and hyperplasia.

EXAMPLE 6

Gelatin capsules, each of which contains 1 mg of N-(1-S-carbethoxy-3-phenyl-propyl)-S-alanyl-1S,3S,5S-2-azabicyclo[3.3.0]octane-3-carboxylic acid, are prepared analogously using 10 mg of active compound.

EXAMPLE 7

The preparation of a solution for injection for the treatment of cardiac and of vascular hypertrophy and hyperplasia is described below

| | |
|---|---|
| N-(1-S-carboxy-3-phenyl-propyl)-S-alanyl-1S,3S,5S-2-azabicyclo[3.3.0]octane-3-carboxylic acid | 250 mg |
| Methylparaben | 5 g |
| Propylparaben | 1 g |
| Sodium chloride | 25 g |
| Water for injections | 5 l |

N-(1-S-carboxy-3-phenyl-propyl)-S-alanyl-1S,3S,5S-2-azabicyclo[3.3.0]octane-3-carboxylic acid, the preservatives and sodium chloride are dissolved in 3 l of water for injections and made up to 5 l with water for injections. The solution is filtered sterile and dispensed aseptically into presterilized bottles, which are closed with sterilized rubber caps. Each bottle contains 5 ml of solution.

EXAMPLE 8

Tablets which can be used for the treatment of cardiac and of vascular hypertrophy and hyperplasia are prepared as described in Example 1, with the exception that, in place of N-(1-S-carbethoxy-3-phenyl-propyl)-S-alanyl-1S,3S,5S-2-azabicyclo[3.3.0]octane-3S-carboxylic acid,
N-(1-S-carboxy-3-phenyl-propyl)-S-alanyl-1S,3S,5S-2-azabicyclo[3.3.0]octane-3-carboxylic acid or
N-(1-S-carboxy-3-phenyl-propyl)-S-alanyl-2S,3aR,7aS-octahydroindole-2-carboxylic acid or
N-(1-S-carbethoxy-3-phenyl-propyl)-S-alanyl-cis-2,3,3a,4,5,7a-hexahydro[1H]indole-2-S-endo-carboxylic acid or
N-(1-S-carboxy-3-phenyl-propyl)-S-alanyl-cis-2,3,4a,4,5,7a-hexahydro[1H]indole-2S-endo-carboxylic acid or
N-(1-S-carboxy-3-phenyl-propyl)-S-lysyl-1S,3S,5S-2-azabicyclo[3.3.0]octane-3-carboxylic acid or
N-(1-S-carbethoxy-3-cyclohexyl-propyl)-S-alanyl-1S,3S,5S-2-azabicyclo[3.3.0]octane-3-carboxylic acid or
N-(1-S-carboxy-3-cyclohexyl-propyl)-S-lysyl-1S,3S,5S-2-azabicyclo[3.3.0]octane-3-carboxylic acid are used.

EXAMPLE 9

A solution for injection is prepared in analogy to the procedure described in Example 7 with the exception that in place of N-(1-S-carbethoxy-3-phenyl-propyl)-S-alanyl-1S,3S,5S-2-azabicyclo[3.3.0]octane-3-carboxylic acid,
N-(1-S-carboxy-3-phenyl-propyl)-S-alanyl-1S,3S,5S-2-azabicyclo[3.3.0]octane-3-carboxylic acid or
N-(1-S-carbethoxy-3-phenyl-propyl)-S-alanyl-2S,3aR,7aS-octahydroindole-2-carboxylic acid hydrochloride or
N-(1-S-carboxy-3-phenyl-propyl)-S-alanyl-2S,3aR,7aS-octahydroindole-2-carboxylic acid or
N-(1-S-carbethoxy-3-cyclohexyl-propyl)-S-alanyl-cis-2,3,3a,4,5,7a-hexahydro[1H]indole-2-S-endo-carboxylic acid or
N-(1-S-carboxy-3-phenyl-propyl)-S-alanyl-cis-2,3,3a,4,5,7a-hexahydro[1H]indole-2-S-endo-carboxylic acid or
N-(1-carboxy-3-phenyl-propyl)-S-lysyl-1S,3S,5S-2-azabicyclo[3.3.0]octane-3-carboxylic acid or
N-(1-S-carbethoxy-3-cyclohexyl)-S-alanyl-1S,3S,5S-2-azabicyclo[3.3.0]octane-3-carboxylic acid or
N-(1-S-carboxy-3-cyclohexyl-propyl)-S-lysyl-1S,3S,5S-2-azabicyclo[3.3.0]octane-3-carboxylic acid are used.

We claim:

1. A method for the treatment of cardiac and of vascular hypertrophy and hyperplasia in mammals comprising the step of administering to a mammal an effective amount of an angiotensin converting enzyme inhibitors of the formula I

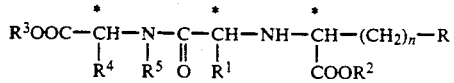

in which
- n is 1 or 2,
- R is hydrogen, alkyl with 1-8 carbon atoms, or aryl which has 6-12 carbon atoms,
- $R^1$ is hydrogen, an aliphatic radical with 1-6 carbon atoms, or the side-chain, which is protected where necessary, of a naturally occurring α-amino acid,
- $R^2$ and $R^3$ are identical or different and are hydrogen, alkyl with 1-6 carbon atoms, aryl with 6-12 carbon atoms or $(C_6-C_{12})$-aryl-$(C_1-C_4)$-alkyl, and
- $R^4$ and $R^5$ form, together with the atoms carrying them, a heterocyclic mono, bi-or tri cyclic ring system with 4 to 15 carbon atoms, or a physiologically tolerated salt thereof.

2. A method for the treatment of cardiac and of vascular hypertrophy and hyperplasia in mammals as claimed in claim 1, wherein $R^4$ and $R^5$ form, together with the atoms carrying them, a heterocyclic bicyclic ring system from the series comprising: tetrahydroisoquinoline, decahydroisoquinoline, octahydroindole and octahydrocyclopentapyrrole.

3. The method as claimed in claim 1, wherein [S,S,S,S,S]-N-(1-carbethoxy-3-phenyl-propyl)-alanyl-octahydroindole-2-carboxylic acid is administered.

4. The method as claimed in claim 1, wherein N-[1-(S)-carbethoxy-3-phenyl-propyl-(S)-alanyl]-2S,3aR,-7aS-octahydroindole-2-carboxylic acid is administered.

5. The method as claimed in claim 1, wherein [S,S,S,S,S]-N-[(1-carbethoxy-3-phenyl-propyl-(S)-alanyl]-decahydroisoquinoline-3-carboxylic acid is administered.

6. The method as claimed in claim 1, wherein [S,S,S,]-N-[(1-carbethoxy-3-phenyl-propyl)-alanyl)-tetrahydroisoquinoline-3-carboxylic acid is administered.

7. The method as claimed in claim 1, wherein (S,S,S,S,S)-N-(1-carbethoxy-3-phenyl-propyl)-alanyl-2-azabicyclo[3.3.0]octane-3-carboxylic acid is administered.

8. The method as claimed in claim 1, wherein N-(1-S-carbethoxy-3-phenyl-propyl)-S-alanyl-cis-endo-2-azabicyclo[3.1.0]hexane-3-S-carboxylic acid is administered.

9. The method as claimed in claim 1, wherein N-(1-S-Carbethoxy-3-phenyl-propyl)-S-alanyl-cis-endo-2,3,3a,4,5,7a-hexahydroindole-2-S-carboxylic acid is administered.

10. The method as claimed in claim 1, wherein, in place of the ethyl esters, the corresponding dicarboxylic acids are administered.

11. The method as claimed in claim 1, wherein the angiotensin converting enzyme inhibitors are administered orally or parenterally.

12. The method as claimed in claim 1, wherein the angiotensin converting enzyme inhibitors are combined with pharmaceutically suitable vehicles and auxiliaries for the forms appropriate for administration.

13. The method as claimed in claim 1 for the treatment of cardiac hypertrophy and hyperplasia.

14. The method as claimed in claim 1 for the treatment of vascular hypertrophy and hyperplasia.

UNITED STATES PATENT AND TRADEMARK OFFICE
CERTIFICATE OF CORRECTION

PATENT NO. : 5,231,083
DATED : July 27, 1993
INVENTOR(S) : Wolfgang Linz et al.

It is certified that error appears in the above-indentified patent and that said Letters Patent is hereby corrected as shown below:

Claim 1, column 12, last line change "itors" to --itor--.

Claim 5, column 14, line 2, change "-(S)-" to --)--.

Claim 6, column 14, line 6, change "tetrahy-" to --tetra--.

Claim 6, column 14, line 7, change "droisoquinoline" to --hydroisoquinoline--.

Claim 9, column 14, line 17, change "Carbethoxy" to --carbethoxy--.

Signed and Sealed this

Twelfth Day of July, 1994

Attest:

BRUCE LEHMAN

Attesting Officer    Commissioner of Patents and Trademarks